US00PP26799P3

(12) United States Plant Patent
Cain

(10) Patent No.: US PP26,799 P3
(45) Date of Patent: Jun. 7, 2016

(54) GRAPEVINE NAMED 'IFG TWENTY'

(50) Latin Name: ***Vitis interspecific* hybrid**
Varietal Denomination: IFG Twenty

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 54 days.

(21) Appl. No.: 14/120,084

(22) Filed: Apr. 25, 2014

(65) Prior Publication Data

US 2015/0313050 P1 Oct. 29, 2015

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Susan McCormick Ewoldt

(57) ABSTRACT

This invention is a new and distinct grapevine variety denominated 'IFG Twenty'. The new grapevine is characterized by producing naturally large seedless blue-black berries having a narrow ellipsoidal to cylindrical shape with a strong fruity labrusca flavor. Fruits normally ripen mid to late season about early to mid-September near Delano Calif. Fruits are fairly low in acidity, with medium dense firm texture, occasionally noticeable seed trace. Vines are productive and can be spur pruned.

1 Drawing Sheet

Latin name of the genus and species claimed: *Vitis interspecific* hybrid.

Variety denomination: 'IFG Twenty'.

BACKGROUND OF THE INVENTION

The new and distinct grapevine described and claimed herein originated from a hand pollinated cross of the IFG 01032-067-222, an unnamed seedless selection from the IFG breeding program, and the Arkansas 2798 (unnamed interspecific) hybridized in May 2006. The abortive seed traces were subsequently embryo cultured and the resulting population of plants was planted in the field in April 2007. The present variety of grapevine was selected as a single plant in September 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Twenty' is characterized by producing naturally large seedless blue-black berries having a narrow ellipsoidal to cylindrical shape with a strong fruity labrusca flavor. Fruits normally ripen mid to late season about early to mid-September near Delano Calif. Fruits are fairly low in acidity, with medium dense, firm texture, with occasionally noticeable seed traces. Attachment of the berry to the pedicel is somewhat weak. The variety stores and ships well and is suitable for long-term storage and long distance shipping. Vines are vigorous, very productive and can be pruned to short spurs.

The new grapevine differs from its maternal parent the IFG 01032-067-222 by having blue-black rather than light red berries and by having a very strong fruity labrusca type flavor as opposed to the neutral flavor of the IFG 01032-067-222. The berries of 'IFG Twenty' are more elongated than the IFG 01032-067-222 and the peduncle is less lignified. 'IFG Twenty' can be distinguished from its pollen parent, A2798, by having a more elongated and less firm berry, by having larger berry and cluster size and by having much better resistance to tip cracking of berries when fully ripe as compared to the A2798.

Grape breeders have used several native American grape species to improve hardiness, disease and insect resistance as well as incorporate aromatic flavors into the vinifera species. Previously introduced interspecific varieties have had very limited commercial success due to small fruit size, large seed traces, slip-skin texture or lack of firmness. The new grapevine variety is being introduced because of its unique combination of late ripening, labrusca flavor combined with firm texture, seedlessness, good adhesion of skin and flesh and naturally large berry size.

BRIEF DESCRIPTION OF THE DRAWING

The accompanying photographic drawing in FIG. 1 illustrates in full color 'IFG Twenty'. The photograph was taken outdoors with indirect lighting. The colors are as nearly true as is reasonably possible in a color representation of this type. The left side of the drawing has a young shoot tip with tendrils and young leaves. A mature fruit cluster is represented in the center of the drawing along with a typical berry in cross section. A mature leaf can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London. England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty' plants grown in the vicinity of Delano, Kern County, Calif. during 2012 and is believed to apply to plants of the variety grown under similar conditions of soil and climate elsewhere:

VINE

General:
- *Vigor*.—Vigorous.
- *Density of foliage*.—Dense.
- *Productivity*.—Very productive, producing about 49 to 74 kg of fruit per vine.
- *Root stock*.—Own root.
- *Training method*.—Typically spur pruned leaving 2 bud spurs.

Trunk:
- *Trunk diameter of* 4-*year-old vines at* 30 *cm above the soil line*.—About 5.7 cm.
- *Shape*.—Stocky to medium.
- *Straps*.—Short — split.
- *Surface texture*.—Medium rough texture.
- *Inner bark color*.—The following colors were observed: Greyed-orange: 177A and 177B.

SHOOTS

Young shoot:
- *Form of tip*.—Wide open.
- *Distribution of anthocyanin coloration of tip*.—Absent.
- *Intensity of anthocyanin coloration of tip*.—Absent.
- *Density of prostrate hairs of tip*.—Medium to dense.
- *Density of erect hairs of tip*.—Absent.
- *Color*.—The following colors were observed: Yellow-green: 144A, and 146B and 146C.

Woody shoot (mature canes):
- *Internode length*.—Medium, about 7.6 cm.
- *Width at node*.—About 2.0 cm.
- *Cross section*.—Elliptic.
- *Surface*.—Striate.
- *Main color*.—The following colors were observed: Greyed-orange: 166A and 166B and 166C and 166D.
- *Density of erect hairs on nodes*.—None.
- *Density of erect hairs on internodes*.—None.
- *Axillary shoot length at full bloom*.—Medium long, approximately 19.2 cm.

Flowering shoot:
- *Vigor during flowering*.—Strong.
- *Attitude during flowering on shoots not tied*.—Semi-drooping to drooping.
- *Color*.—Dorsal side of internodes — Yellow-green: 146C, with Red-purple stripes: 59B.
- *Color*.—Ventral side of internodes — Yellow-green: 146C.
- *Color*.—Dorsal side of nodes — Yellow-green: 146C.
- *Color*.—Ventral side of nodes — Yellow green: 146C.
- *Density of prostrate hairs of nodes*.—Very sparse.
- *Density of erect hairs of nodes*.—Very sparse.
- *Density of prostrate hairs on internode*.—None.
- *Density of erect hairs on internode*.—None.
- *Anthocyanin coloration of buds*.—Absent.

Tendrils:
- *Distribution on the shoot* (*at full flowering*).—Discontinuous.
- *Length of tendril*.—Medium, about 16.9 cm.
- *Thickness of tendril* 2 *cm from base*.—About 1.6 mm.
- *Color*.—The following colors were observed: Yellow-green: N144A and N144C, and 146B and 146C.
- *Form*.—Trifurcated.
- *Number of consecutive tendrils*.—2.

LEAVES

Young leaves:
- *Color of upper surface of first four distal unfolded leaves*.—Yellow-green: 146C.
- *Average intensity of anthocyanin coloration of six distal leaves prior to flowering*.—Absent.
- *Density of prostrate hairs between veins* (*lower surface*).—Very sparse.
- *Density of prostrate hairs on veins* (*lower surface*).—Very sparse.
- *Density of erect hairs between veins* (*lower surface*).—Absent.
- *Density of erect hairs on veins* (*lower surface*).—Sparse.

Mature leaves:
- *Average length*.—About 14.5 cm.
- *Average width*.—About 18.0 cm.
- *Mature leaf size*.—Medium large.
- *Shape of blade*.—Wedge-shaped.
- *umber of lobes*.—5.
- *Anthocyanin coloration of main veins on upper side of blade*.—Absent to very weak.
- *Mature leaf profile*.—Undulate.
- *Blistering surface of blade upper surface*.—Very weak.
- *Leaf blade tip*.—In the plane of the leaf.
- *Undulation of margin*.—Medium.
- *Undulation of blade between main and lateral veins*.—Overall.
- *Shape of teeth*.—Mixture of both sides straight and both sides convex.
- *Length of teeth*.—Medium.
- *Ratio length/width of teeth*.—Medium.
- *Shape of upper lateral sinuses*.—Closed to lobes slightly overlapping.
- *Depth of upper lateral sinuses*.—Shallow.
- *General shape petiole sinus*.—Half open to slightly open.
- *Shape of base of upper leaf sinuses*.—U-shaped.
- *Tooth at petiole sinus*.—Absent.
- *Density of prostrate hairs between veins on lower surface of blade*.—Absent to very sparse.
- *Density of erect hairs between veins on lower surface of blade*.—Absent.
- *Density of prostrate hairs on main veins on lower surface of blade*.—Sparse.
- *Density of erect hairs on main veins on lower surface of blade*.—Sparse to medium.
- *Density of prostrate hairs on main veins on upper surface of blade*.—Very sparse.

*Density of erect hairs on main veins on upper surface of blade*.—None.

*Autumn coloration of leaves*.—Leaves can be a single color or combination of colors, in a mottled pattern or on the edges of the leaves. The following colors were observed: Yellow: 13A and 13B; and Greyed-orange: 175A; and Greyed-purple: 183A and 183B.

Upper surface:

*Color*.—The following colors were observed: Green: 137A and 137B.

*Anthocyanin coloration of main veins*.—Absent.

*Surface appearance*.—Dull.

*Blistering surface of blade*.—Very weak

Lower surface:

*Color*.—The following colors were observed: Green: 138A and 138B.

*Anthocyanin coloration of main veins* (*lower surface*).—Absent

*Glossiness*.—Weak.

*Surface texture*.—Smooth.

*Surface appearance*.—Dull.

Petiole:

*Length*.—About 12.5 cm.

*Length of petiole compared to middle vein*.—Slightly shorter.

*Density of prostrate hairs on petiole*.—None.

*Density of erect hairs on petiole*.—None.

Buds:

*Bud fruitfulness*.—Basal: mostly fruitful.

*Position of first fruitful shoot on previous season cane*.—$1^{st}$ to $3^{rd}$ node.

*Dormant bud length*.—About 4.9 mm.

*Dormant bud width in the proximal/distal plane*.—About 6.1 mm.

*Dormant bud color*.—Greyed-orange: 166A.

*Time of bud burst*.—Midseason; about Mar. 15, 2012.

FLOWERS

General:

*Flower sex*.—Hermaphrodite.

*Length of first inflorescence*.—Medium to long, about 25.5 cm long by 13.3 cm wide.

*Position of first flowering and fruiting node*.—$4^{th}$ to $5^{th}$ node (current season growth).

*Number of inflorescence per flowering shoot*.—1.1 to 2.

*Time of bloom*.—Late as compared with similar varieties in the growing area of Delano, Calif.

*Date of full bloom*.—About May 18, 2012.

FRUIT

General:

*Ripening period*.—Mid to late season: approximately Sep. 18, 2012.

*Use*.—Fresh market.

*Keeping quality*.—Excellent, remains commercially acceptable when stored up to 8 weeks at 0° C. and high RH.

*Resistance to*.—Insects: Average typical of *Vitis vinifera* species. Diseases: Average typical of *Vitis vinifera* species.

*Refractometer test*.—Soluble solids: about 18.6 Brix.

*Brix/acid*.—About 38.0.

*Titratable acidity*.—About 0.19.

*Juice pH*.—About 3.64.

Cluster:

*Mature cluster length* (*peduncle excluded*).—About 35.6 cm.

*Mature cluster width*.—About 17.8 cm.

*Mature cluster weight*.—About 1236 g.

*Bunch density*.—Loose to medium loose.

*Number of berries*.—About 208.

*Form*.—Conical.

Peduncle:

*Lignification of peduncle*.—Weak.

*Length of peduncle*.—Medium long, approximately 2.2 cm.

Berry:

*Uniformity of size*.—Uniform.

*Single berry weight*.—About 6.6 g natural to about 7.9 g when treated with gibberellic acid.

*Shape*.—Narrow ellipsoidal to cylindrical.

*Seeds*.—Seed traces occasionally noticeable.

*Cross section*.—Circular.

*Berry dimensions*.—Longitudinal axis: about 2.7 cm; horizontal axis: about 1.9 cm.

*Berry firmness*.—Medium firm.

*Particular flavor*.—Labrusea.

*Bloom* (*cuticular wax*).—Medium to heavy.

*Berry separation from pedicel*.—Medium to easy.

*Skin color* (*without bloom*).—The following colors were observed: Greyed-purple: N186B and N186C.

*Flesh color*.—Yellow-green: 152B.

Skin:

*Thickness*.—Medium.

*Skin toughness*.—Somewhat notable when chewing.

*Reticulation*.—Absent.

*Tenacity*.—Tenacious to flesh.

What is claimed:

1. A new and distinct variety of grapevine as herein illustrated and described.

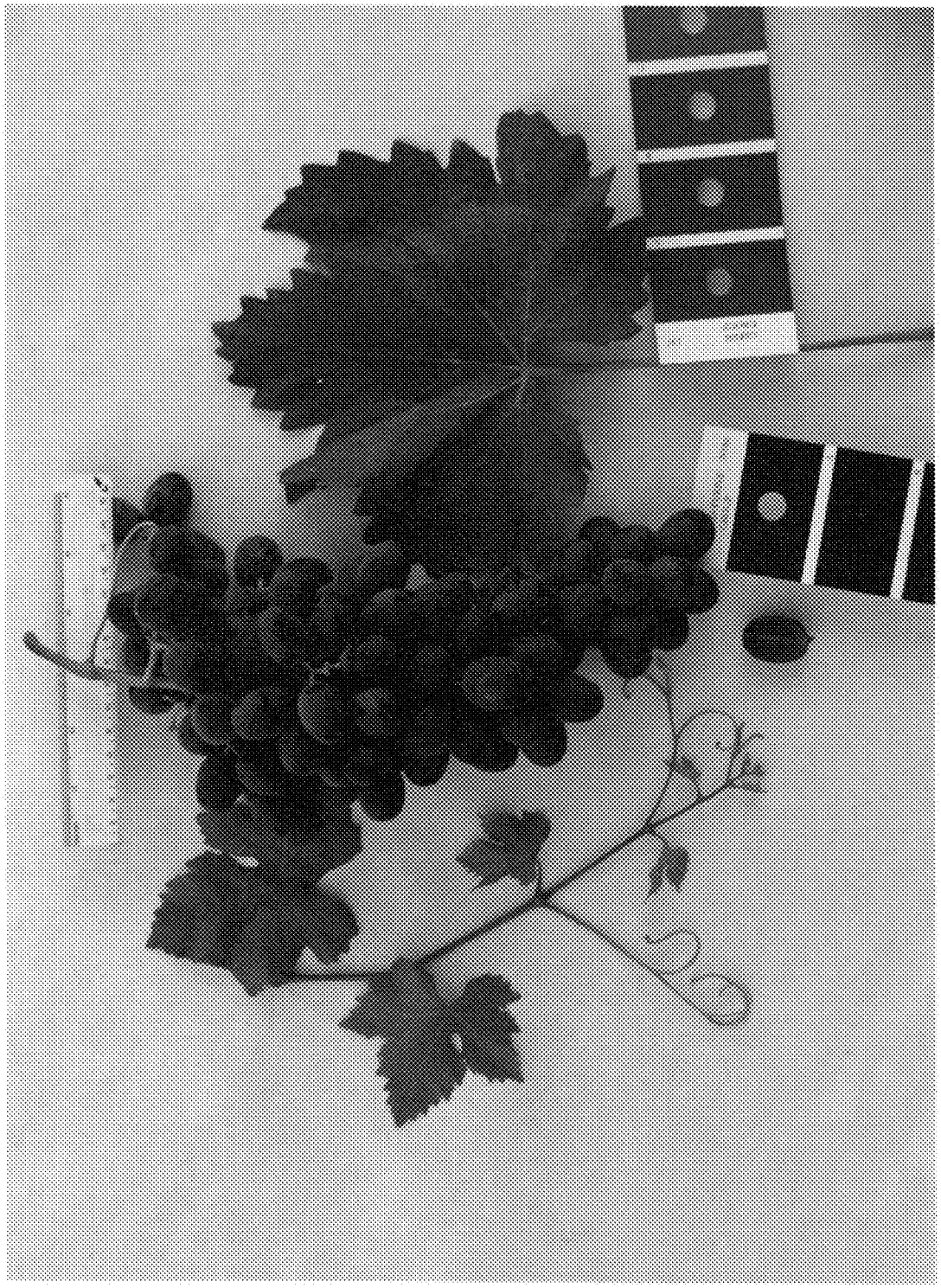

* * * * *